(12) United States Patent
Christensen et al.

(10) Patent No.: US 7,108,832 B2
(45) Date of Patent: Sep. 19, 2006

(54) STERILIZATION METHODS AND APPARATUS WHICH EMPLOY ADDITIVE-CONTAINING SUPERCRITICAL CARBON DIOXIDE STERILANT

(75) Inventors: Timothy Wayne Christensen, Ithaca, NY (US); David Carroll Burns, Ithaca, NY (US); Angela Lydia White, Truxton, NY (US); Bruce Ganem, Ithaca, NY (US); Anthony Romey Eisenhut, Lansing, NY (US)

(73) Assignee: NovaSterilis Inc., Ithaca, NY (US)

( * ) Notice: Subject to any disclaimer, the term of this patent is extended or adjusted under 35 U.S.C. 154(b) by 0 days.

(21) Appl. No.: 10/869,052

(22) Filed: Jun. 17, 2004

(65) Prior Publication Data

US 2005/0025667 A1 Feb. 3, 2005

Related U.S. Application Data

(60) Provisional application No. 60/480,410, filed on Jun. 23, 2003.

(51) Int. Cl.
*A61L 2/00* (2006.01)

(52) U.S. Cl. ............................ 422/28; 422/28; 422/31; 422/33; 422/119; 422/297; 516/9

(58) Field of Classification Search .................... 134/1; 204/157.15, 158.2; 422/28, 31, 33, 119, 422/297; 516/9
See application file for complete search history.

(56) References Cited

U.S. PATENT DOCUMENTS

| | | | | |
|---|---|---|---|---|
| 4,944,837 A | * | 7/1990 | Nishikawa et al. | 216/41 |
| 5,213,619 A | * | 5/1993 | Jackson et al. | 134/1 |
| 5,370,740 A | * | 12/1994 | Chao et al. | 134/1 |
| 5,851,483 A | * | 12/1998 | Nicolle et al. | 422/28 |
| 5,996,155 A | * | 12/1999 | Chao et al. | 8/158 |
| 6,149,864 A | | 11/2000 | Dillow et al. | |
| 6,518,307 B1 | * | 2/2003 | McKenzie et al. | 514/557 |
| 6,613,278 B1 | | 9/2003 | Mills et al. | |
| 6,716,457 B1 | * | 4/2004 | Eagles et al. | 424/616 |
| 2003/0072677 A1 | | 4/2003 | Kafesjian et al. | |
| 2004/0033269 A1 | * | 2/2004 | Hei et al. | 424/616 |
| 2004/0120852 A1 | | 6/2004 | Kanno | |

OTHER PUBLICATIONS

Holyoak et al, "Toxic effects of ethylene oxide residuals on bovine embryos in vitro", TOXICOLOGY, 108, 1996, pp. 33-38.

Cornu et al, "Effect of Freeze-Drying and Gamma Irradiation on the Mechanical Properties of Human Cancellous Bone", Journal of Orthopaedic Research, vol. 18, No. 3, 2000, pp. 426-431.

Spilimberrgo et al, "Microbial inactivation by high-pressure", Journal of Supercritical Fluids, 22, 2002, pp. 55-63.

Akkus et al, "Fracture resistance of gamma radiation sterilized cortical bone allografts", Journal of Orthopaedic Research, 19, 2001, pp. 927-934.

(Continued)

*Primary Examiner*—Krisanne Jastrzab
(74) *Attorney, Agent, or Firm*—Welsh & Flaxman LLC

(57) ABSTRACT

Sterilization methods and apparatus are effective to achieve a 6-log reduction in CFUs of industry standard bacteria and bacterial spores, i.e., *B. stearothermophilus* and *B. subtilis* spores, by subjecting sterilizable materials to a chemical additive-containing carbon dioxide sterilant fluid at or near its supercritical pressure and temperature conditions. Most preferably, the chemical additive-containing supercritical carbon dioxide sterilant fluid is agitated during sterilization, e.g., via mechanical agitation or via pressure cycling.

9 Claims, 2 Drawing Sheets

OTHER PUBLICATIONS

Jahan et al, "Long-Term Effects of Gamma-Sterialization on Degradation of Implant Materials", Appl. Radiat. Isot., vol. 46, No. 6/7, 1995, pp. 637-638.

Ikarashi et al, "Cytotoxicity of medical materials sterilized with vapour-phase hydrogen peroxide", BIOMATERIALS, vol. 16, No. 3, 1995, pp. 177-183.

Duffy et al, "An Epidemic of Corneal Destruction Caused by Plasma Gas Sterilization", Arch. Ophthalmol., vol. 118, Sep. 2000, pp. 1167-1176.

Godette et al, "Biomechanical Effects of Gamma Irradiation on Fresh Frozen Allografts in Vivo", ORTHOPEDICS, vol. 19, No. 8, Aug. 1996, pp. 649-653.

Schiewe et al, "Toxicity Potential of Absorbed-Retained Ethylene Oxide Residues in Culture Dishes on Embryo Development in Vitro", Journal of Animal Science, vol. 60, No. 6, 1985, pp. 1610-1618.

Windebank et al, "Residual Ethylene Oxide in Hollow Fiber Hemodialysis Units Is Neurotoxic in Vitro", Annals of Neurology, vol. 26, No. 1, Jul. 1989, pp. 63-68.

\* cited by examiner

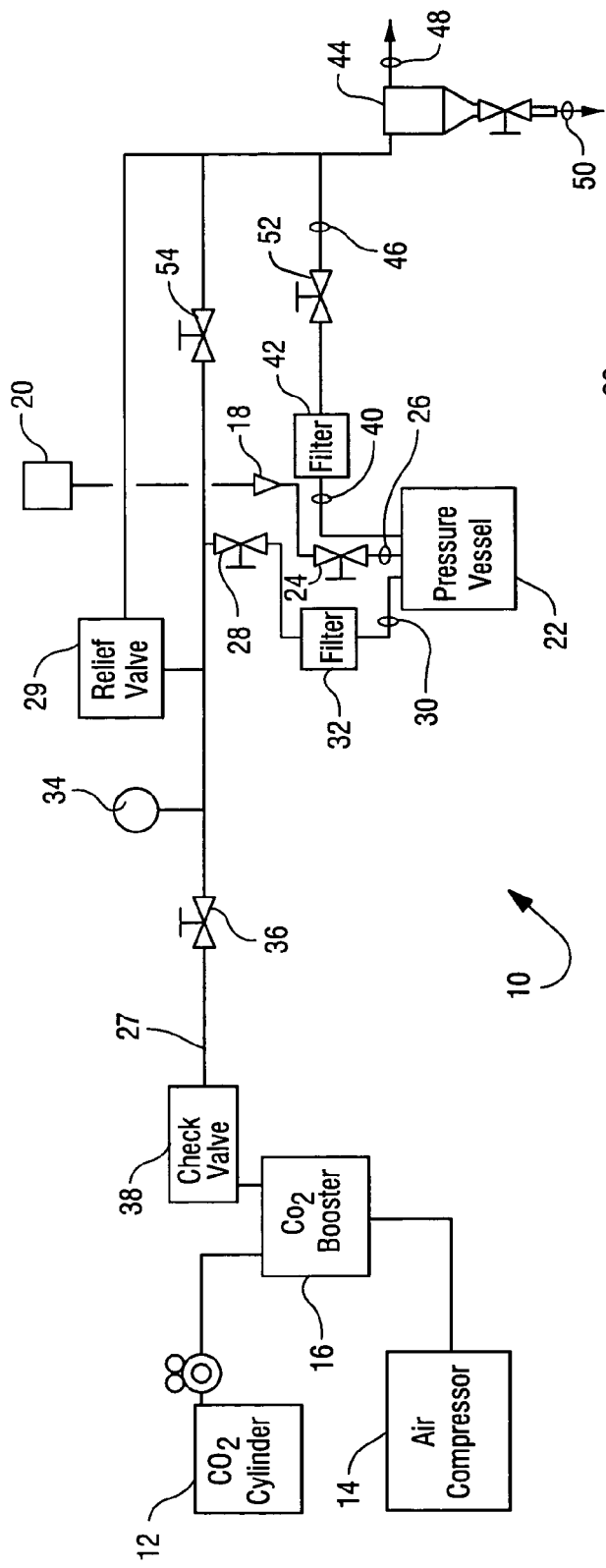
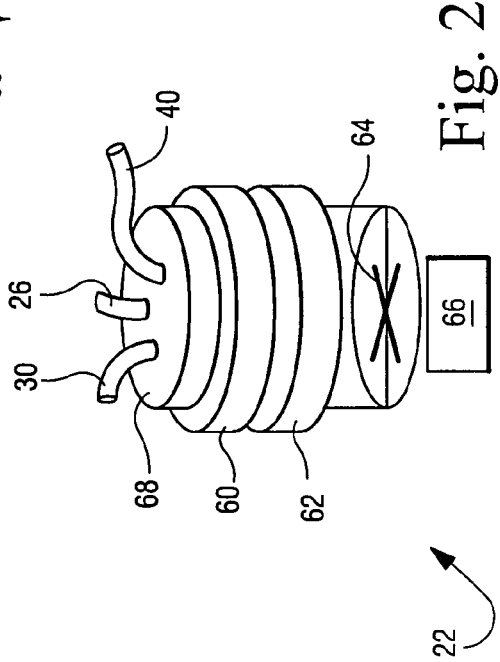
Fig. 1
Fig. 2

STERILIZATION METHODS AND APPARATUS WHICH EMPLOY ADDITIVE-CONTAINING SUPERCRITICAL CARBON DIOXIDE STERILANT

CROSS REFERENCE TO RELATED APPLICATION

This application is based on, and claims domestic priority benefits under 35 U.S.C. §119(e) from, Provisional Application No. 60/480,410, filed Jun. 23, 2003, the entire content of which is hereby incorporated by reference.

FIELD OF THE INVENTION

The present invention relates generally to sterilization methods and apparatus in which supercritical carbon dioxide is employed as a sterilization fluid. In especially preferred embodiments, the present invention relates to methods and apparatus in which the efficacy of the supercritical carbon dioxide is enhanced by certain chemical additives.

BACKGROUND OF THE INVENTION

A need has developed in the tissue implantation or transplantation, biomedical polymers, medical equipment, and drug delivery industries for a gentle and reliable sterilization method that results in greater than $10^6$ log reductions of microbial and viral contaminants without impacting the properties of the material being sterilized. Indeed many new medical advances cannot be implemented because the sterilization industry is unable to provide a suitable sterilant as part of the manufacturing process.

In the case of polymers, gamma irradiation has been shown to compromise the mechanical properties.[1] Furthermore, steam sterilization is incompatible with thermally or hydrolytically labile polymers. Ethylene oxide, a common and widely used sterilant, is toxic, mutagenic, and a carcinogenic substance that can react with some polymers, and also requires prolonged periods of outgassing.

[1]Jahan et al, "Long-term effects of gamma-sterilization on degradation of implant materials." *Applied Radiation and Isotopes: Including Data, Instrumentation and Methods For Use in Agriculture, Industry and Medicine* 46(6–7): 637–8 (1995), incorporated expressly hereinto by reference.

Biological tissues, including macromolecular biopolymers, are also incompatible with steam. Gamma radiation results in a significant decrease in tissue integrity and bone strength.[2] Certain antibacterial washes have been used to disinfect tissue, but incomplete sterilization is achieved and the washes leave residual toxic contaminants in the tissues.[3] Ethylene oxide also reacts with biological tissue and is thus an undesirable sterilant for such reason.

[2] Cornu et al, "Effect of freeze-drying and gamma irradiation on the mechanical properties of human cancellous bone", Journal of Orthopaedic Research, 18(3), p. 426–31 (2000); and Akkus et al, "Fracture resistance of gamma radiation sterilized cortical bone allografts." *Journal of Orthopaedic Research: Official Publication of the Orthopaedic Research Society* 19(5): 927–34 (2001), the entire content of each incorporated expressly hereinto by reference.
[3]Holyoak et al, "Toxic effects of ethylene oxide residues on bovine embryos in vitro", Toxicology, 108(1–2, p. 33–8 (1996), the entire content of each incorporated hereinto by reference.

Many medical devices, such as stents, catheters and endoscopes, are fabricated from, or coated with, sensitive polymers that cannot tolerate steam, irradiation, or ethylene oxide. Plasma sterilization has been shown to be incompatible with some medical equipment and leaves toxic residues (Ikarashi, Tsuchiya et al. 1995; Duffy, Brown et al. 2000).[4]

[4]Ikarashi et al, "Cytotoxicity of medical materials sterilized with vapourphase hydrogen peroxide." *Biomaterials* 16(3): 177–83 (1995) and Duffy et al, "An epidemic of corneal destruction caused by plasma gas sterilization. The Toxic Cell Destruction Syndrome Investigative Team." *Archives of Ophthalmology* 118(9): 1167–76 (2000), the entire content of each expressly incorporated hereinto by reference.

Recently, in U.S. Pat. No. 6,149,864 to Dillow et al (the entire content of which is expressly incorporated hereinto by reference), the use of supercritical $CO_2$ was disclosed as an alternative to existing technologies for sterilizing a wide range of products for the healthcare industry with little or no adverse effects on the material treated.

Specifically, the Dillow '864 patent disclosed the inactivation of a wide range of vegetative microbial cells using supercritical carbon dioxide with agitation and pressure cycling. However, only one spore-forming bacterium was investigated in the Dillow '864 patent, specifically, *B. cereus*. No disclosure appears in Dillow '864 patent regarding the efficacy of the therein suggested techniques using currently accepted bio-indicator standards used to judge sterilization (i.e., *B. stearothermophilus* and *B. subtilis*). Subsequently, however, other investigators achieved only a 3.5 log reduction in *B. subtilis* spores using the method disclosed in the Dillow et al '864 patent.[5]

[5]Spilimbergo et al, "Microbial inactivation by high-pressure." *J. Supercritical Fluids* 22: 55–63 (2002), the entire content expressly incorporated hereinto by reference.

Bacterial spores are more difficult to sterilize than vegetative cells. *B. stearothermophilus* and *B. subtilis* spores represent the greatest challenge to sterilization methods (FDA 1993) and are the currently accepted standards within the industry for validating sterilization methods. Sterilization is defined as greater than or equal to 6-log ($10^6$) reduction in colony forming units (CFUs). Reproducible inactivation of these resistant microbes is required for commercialization of novel sterilization equipment and processes.

It therefore would be highly desirable if sterilization methods and apparatus could be provided which are effective to achieve a 6-log reduction in CFUs of industry standard bacterial spores. It would more specifically be especially desirable if sterilization methods and apparatus could be provided that achieve a 6-log reduction in CFUs of *B. stearothermophilus* and *B. subtilis* spores. The present invention is therefore directed to fulfilling such needs.

SUMMARY OF THE INVENTION

Broadly, sterilization methods and apparatus are provided by the present invention which are effective to achieve a 6-log reduction in CFUs of industry standard bacterial spores. More specifically, according to the present invention, sterilization methods and apparatus are provided which are effective to achieve a 6-log reduction in CFUs of *B. stearothermophilus* and *B. subtilis* spores. These 6-log reductions are achieved by the present invention by subjecting sterilizable materials under sterilization pressure and temperature conditions using a chemical additive-containing supercritical carbon dioxide as a sterilant fluid. Most preferably, the chemical additive-containing supercritical carbon dioxide sterilant fluid is agitated during sterilization.

The apparatus and methods of the present invention are especially well suited for the sterilization of thermally or hydrolytically sensitive, medically-important materials, including biodegradable and other medical polymers, tissue for implantation or transplantation, medical equipment, drugs and drug delivery systems. Most preferably, such materials are sterilized by treatment with a chemical addi tive-containing carbon dioxide sterilant at or near its supercritical pressures and temperatures.

Sterilization is specifically further enhanced by imparting turbulence or agitation to the sterilant fluid either mechanically or by means of pressure cycling (see, the above-cited Dillow et al '864 patent). Process variables depend on the material being sterilized. The improved method enhances the mass transfer and sterilization capabilities of supercritical carbon dioxide. Medically useful log reductions ($>10^6$) in microbial contaminants are realized for a range of resistant bacteria, their vegetative forms, and spores, especially bacteria and bacterial spores which are traditionally known to be the hardest to inactivate, such as *B. stearotheromophilus, B. pumilus* and/or *B. subtilis* and spores. Thus, as used herein the term "sterilization" is meant to refer to at least a 6-log ($>10^6$) reduction of industry standard bacteria and related bacterial spores selected from *B. stearotheromophilus, B. pumilus* and/or *B. subtilis*. Thus, a "sterile" surface or article is one which has at least a 6-log ($>10^6$) reduction of such bacteria and spores following a sterilization treatment, as compared to the surface or article prior to such sterilization treatment.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIG. 1 is a schematic view of a presently preferred sterilization apparatus in accordance with the present invention;

FIG. 2 is a detailed schematic view of the pressure vessel employed in the apparatus of FIG. 1.

DETAILED DESCRIPTION OF THE INVENTION

Figure 3:
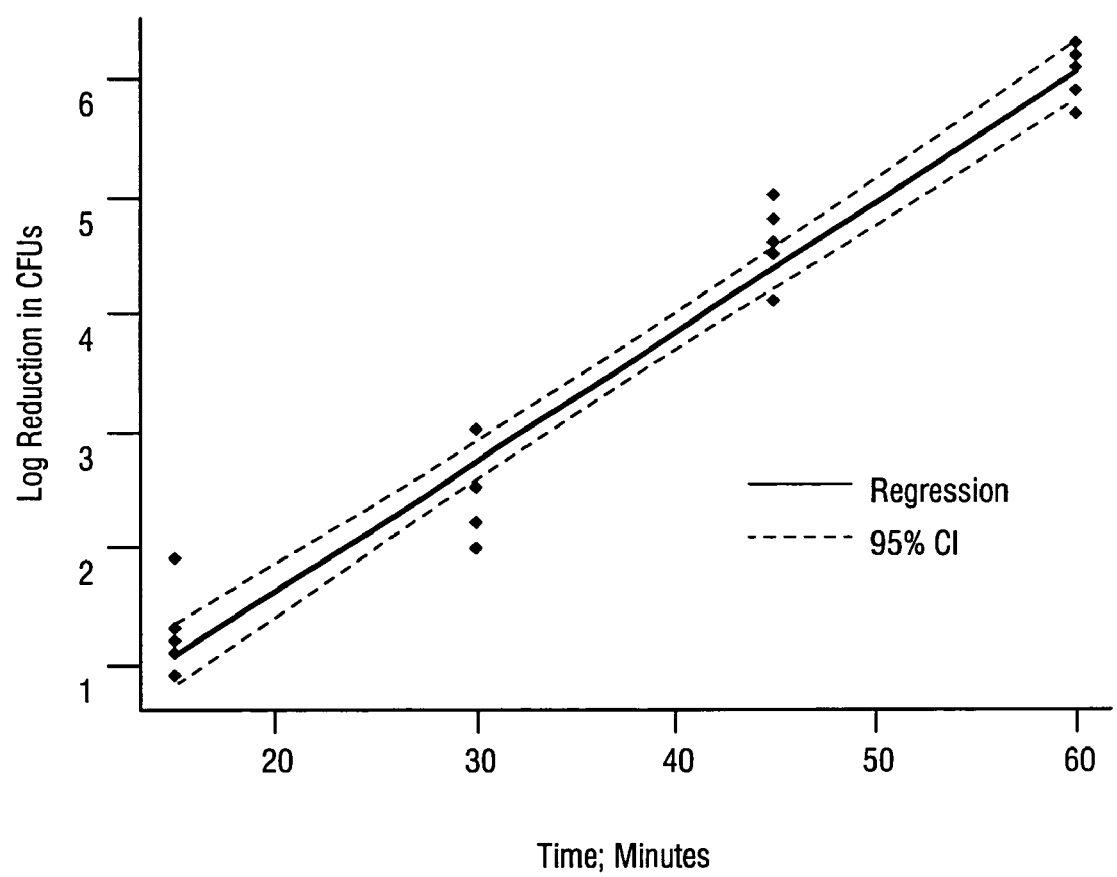
FIG. 3 is a graph of the log reduction in CFU's of *B. stearothermophilus* spores versus time obtained from the data of Example 8 below and shows the linearity of inactivation achieved by means of the present invention.

The sterilization apparatus and methods of the present invention are usefully employed to sterilize a variety of materials, biological tissues, instruments, and devices that are thermally or hydrolytically unstable, or otherwise incompatible with conventional sterilization techniques, or where such techniques are not preferred. Examples of materials that may be sterilized by the present invention include, but are not limited to, biodegradable polymers such as poly(lactic acid) (PLA) or poly(lactic-co-glycolic acid) (PLGA)-based polymers, which can be used in various embodiments as implantable drug delivery devices; tissues for implantation or transplantation, including but not limited to, bone, cartilage, ligament, or other connective or musculoskeletal tissue for allografts in the treatment of orthopaedic trauma and joint reconstruction; grafted or artificial skin tissue for the treatment of burns and other dermal abrasions or damage; medical devices, such as cardiac or urological stents and catheters, including drug- or gene-coated stents and catheters, rigid and flexible endoscopes for orthopaedic, plastic, and gastroenterological surgery; drug delivery devices, including, but not limited to, implantable polymer devices, polymer microspheres, or other specifically shaped drug-releasing devices comprised of PLA, PLGA, or other biodegradable polymers, and drugs in solid or liquid forms (i.e., any substance or active agent used in the diagnosis, treatment or prevention of a disease or illness).

As noted previously, 6-log reductions in CFUs may be achieved in accordance with the present invention by subjecting materials to be sterilized under sterilization temperature and pressure conditions using a chemical additive-containing supercritical carbon dioxide as a sterilant fluid, and especially where the sterilant fluid is agitated during the sterilization process.

Most preferably, the sterilant is carbon dioxide at or near its supercritical pressures and temperature conditions. Thus, the sterilization process of the present invention is practiced using carbon dioxide as a sterilant at pressures between about 1000 to about 3500 psi, at temperatures in the range between about 25° C. to about 60° C. Most preferably, the article to be sterilized is subject to carbon dioxide at or near such pressure and temperature conditions for times ranging from about 20 minutes to about 12 hours. The carbon dioxide employed in the practice of the present invention is most preferably substantially pure. Thus, trace amounts of other gases may be tolerated provided that the sterilization properties of the carbon dioxide are not impaired. For ease of further discussion below, the term "supercritical carbon dioxide" will be used, but it will be understood that such a term is non-limiting in that carbon dioxide within the pressure and temperature ranges as noted immediately above may be employed satisfactorily in the practice of the present invention.

The chemical additives employed in the present invention most preferably include peroxides and/or carboxylic acids. Preferred carboxylic acids include alkanecarboxylic acids and/or alkanepercarboxylic acids, each of which may optionally be substituted at the alpha carbon with one or more electron-withdrawing substituents, such as halogen, oxygen and nitrogen groups. Particularly preferred species of chemical additives employed in the practice of the present invention include hydrogen peroxide (H2O2), acetic acid (AcA), peracetic acid (PAA) and trifluoroacetic acid (TFA), and mixtures thereof. One particularly preferred liquid additive that may be employed in the practice of the present invention is commercially available Sporeclenz® sterilant which is a mixture of acetic acid with hydrogen peroxide and peracetic acid.

The chemical sterilization additive is employed in a sterilization enhancing effective amount of at least about 0.001 vol. % and greater, based on the total volume of the carbon dioxide. The amount of sterilization additive will be dependent upon the particular sterilization additive that is employed. Thus, for example, peracetic acid may be present in relatively small amounts of about 0.005 vol. % and greater, while acetic acid may need to be employed in amount of about 1.0 vol. % and greater. Thus, a range of at least about 0.001 vol. % and greater, up to about 2.0 vol. % will typically be needed in order to achieve a sterilization enhancing effect in combination with carbon dioxide.

One presently preferred embodiment of an apparatus 10 according to the present invention is depicted in accompanying FIGS. 1 and 2. In this regard, it can be seen that the apparatus includes a standard compressed gas cylinder 12 containing carbon dioxide, and a standard air compressor 14 used in operative association with a carbon dioxide booster 16 (e.g., Haskel Booster AGT 7/30). Alternatively, the air compressor 14 and booster 16 can be replaced with a single carbon dioxide compressor.

An additive cycle is also provided by means of a series of an inlet port 18 which allows additive contained in reservoir 20 to be added to a pressure vessel 22 through valve 24 and additive line 26. The carbon dioxide is introduced to the pressure vessel 22 from header line 27 via valve 28 and $CO_2$ supply line 30. A filter 32 (e.g., a 0.5 micron filter) is provided in the supply line 30 to prevent escape of material from the vessel. A pressure gauge 34 is provided downstream of $CO_2$ shut-off valve 36 in supply header 27 to allow the pressure to be visually monitored. A check valve 38 is provided in the line 27 upstream of the valve 36 to prevent reverse fluid flow into the booster 16. In order to prevent an overpressure condition existing in line 27, a pressure relief valve 9 may be provided.

An outlet line 40 through valve 52 allows the pressure vessel 22 to be depressurized. In this regard, the depressurized fluid exits the vessel 22 via line 40, is filtered by filter unit 42 and then is directed to separator 44 where filtered $CO_2$ gas may be exhausted via line 48, and liquid additive collected via line 50 for possible reuse. Valves 52, 54 may be provided in lines 46 and 27, respectively, to allow fluid isolation of upstream components.

The reactor vessel 22 is most preferably constructed of stainless steel (e.g., 316 gauge stainless steel) and has a total internal volume sufficient to accommodate the materials being sterilized either on a laboratory or commercial scale. For example, in laboratory studies, an internal volume of 600 mL (e.g., approximately 8 inches long by about 2.5 inches inside diameter) was deemed adequate As is perhaps more clearly shown in FIG. 2, the pressure vessel 22 includes a vibrator 60, a temperature control unit 62, and a mechanical stirring system most preferably comprised of an impeller 64 and a magnetic driver 66. The reactor vessel 22 contains a conventional basket (not shown) which is also preferably constructed of 316 gauge stainless steel. The basket serves to hold the items to be sterilized as well as to protect the impeller 64 and direct the sterilant fluid in a predetermined manner.

The reactor vessel 22 may be operated at a constant pressure or under continual pressurization and depressurization (pressure cycling) conditions without material losses due to splashing or turbulence, and without contamination of pressure lines via back diffusion. The valves 24, 28 and 52 allow the vessel 22 to be isolated and removed easily from the other components of the apparatus 10. The top 68 of the pressure vessel 22 may be removed when depressurized to allow access to the vessel's interior.

In use, the material to be sterilized is introduced into the interior space of the pressure vessel 22 along with any initial portion of liquid sterilization additive from reservoir 20. The temperature control unit 62 is operated so as to set the desired initial temperature for sterilization. The vessel 22 may then be pre-equilibrated with carbon dioxide from gas cylinder 12 at atmospheric pressure, following which the magnetic driver 66 is operated so as to activate the impeller 64. The pressure vessel 22 may thereafter be pressurized to a desired pressure by introducing additional carbon dioxide gas from cylinder 12 via the air compressor 14 linked to booster 16.

In order to effect a pressure cycling of the vessel 22, an amount of carbon dioxide may be released therefrom via depressurization line by momentarily opening valve 52 sufficient to partially reduce pressure within the vessel 22. Additive may be introduced into the vessel 22 for any given pressure cycle by opening valve 24 which allows liquid additive to flow from reservoir 20 into inlet port 18. It will be understood that the sterilization additives may be introduced prior to pressurization and/or during pressure cycling. Prior to pressurization, additives are introduced directly into the reactor vessel 22 prior to sealing and/or via the additive port 18. The sterilization additives are most preferably introduced during the cycling stages by measured addition to the additive port 18 at ambient pressures. The port 18 is subsequently sealed and the additive chamber is pressurized so that the additive may enter the reactor vessel 22 without altering the internal pressure. The exact mechanism of addition may be modified such that the process is more efficient and/or convenient.

Following additive introduction, the vessel 22 may be repressurized to a desired pressure following introduction of the liquid additive therein. Such depressurization/repressurization with introduction of liquid additive may be repeated for any number of cycles that may be desired. The cycle of depressurization and repressurization as well as the introduction of the carbon dioxide and liquid additive may be automatically controlled via a controller (not shown) which sequences the various valves discussed previously so as to achieve the desired pressure conditions and cycles.

Most preferably, periodic agitation to the contents of vessel 22 is effected using vibrator 60 through the entire process. Intermittent or continuous agitation of the reactor vessel and its contents is performed by vibrating the reactor vessel during sterilization. Agitation enhances mass transfer of the carbon dioxide and additives by eliminating voids in the fluid such that the material being sterilized comes into more complete contact with sterilant. The specific means of agitation may be adjusted to accommodate the particular apparatus employed and to optimize sterilization times, temperatures, and pressure cycles. When sterilization is complete, the vessel 22 is depressurized, the magnetic drive 66 is stopped thereby stopping the stirring impeller 64, and the thus sterilized material removed by opening top 68 of vessel 22.

Although the precise mechanism by which the present invention enhances sterilization is not entirely understood at this time it is theorized that, in conjunction with near-critical or supercritical carbon dioxide, the chemical sterilization additives employed in the present invention likely enhance sterilization by increasing the acidity of the interior of the bacterial cell, especially in the presence of water. Moreover, additives may enhance the permeability of the cell to carbon dioxide, irreversibly inhibit essential cellular processes, and/or extract components required for cell viability, all of which could possibly contribute to enhancements in sterilization that have been observed.

The present invention will be further understood after careful consideration is given to the following Examples.

EXAMPLE 1

The effects of using an additive in accordance with the present invention was compared using the method described by U.S. Pat. No. 6,149,864 to Dillow et al for inactivating *B. stearothermophilus* spores. Specifically, as noted in Table 1 below, the most extreme sterilizations conditions as disclosed in the Dillow et al '864 patent were employed and resulted in only a 1 log reduction in CFUs/mL for the experiment in which no additive was employed (Ex. A). In contrast, a greater than 6 log reduction was achieved using the method of the present invention (Ex. B). The additive was placed on a cotton ball and inserted in the chamber prior to closure. No further additive was used.

|  | Additive | Pressure range psi | # cycles | Agitation Random/ Directional | Temp °C. | Time hrs | Initial CFU/ml | Final CFU/ml | Log Reduction |
|---|---|---|---|---|---|---|---|---|---|
| Ex. A. | Water | 1500–3000 | 3 | +/− | 60 | 2 | $2.3 \times 10^6$ | $2.1 \times 10^5$ | 1.0 |
| Ex. B | Water + TFA | 1100–3000 | 3 | +/+ | 60 | 2 | $2.3 \times 10^6$ | 0* | 6.4 |

*confirmed by turbidity test

EXAMPLE 2—INVENTION

The apparatus generally depicted in FIGS. 1 and 2 was employed for this Example. A sample of *B. stearothermophilus* spores (1 mL) of greater than $10^6$ CFU/mL was placed in 16 mm diameter test tubes in a stainless steel basket. Trifluoroacetic acid (4 mL) was transferred by syringe onto the surface of a cotton ball placed in the basket and water (6 mL) was placed at bottom of vessel. The basket was then loaded into the 600 mL reactor vessel. The reactor vessel was heated to 50° C. and equilibrated with $CO_2$ at atmospheric pressure. The stirring and agitation mechanisms were activated and the reactor vessel pressurized to 2000 psi for 40 minutes. The $CO_2$ pressure was then allowed to drop to 1100 psi at a rate of 300 psi/minute. Agitation by means of vibration of the vessel was carried out for 1 minute.

The pressurization/stirring/agitation/depressurization process was repeated a total of three times. After the third cycle, a series of three flushing cycles to remove the additive was performed by pressurizing and partial de-pressurizing the reactor vessel using $CO_2$. The stirring was stopped and the basket was removed from the reactor vessel. The residual CFUs were counted after serial dilution and culturing of both treated and untreated controls.

Complete kill of bioindicators were achieved over multiple experimental evaluations. These reductions correspond to a log reduction in CFUs of between 6.2 to 6.9.

EXAMPLE 3A—INVENTION

The apparatus generally depicted in FIGS. 1 and 2 was employed for this Example. A sample of *B. subtilis* spore/vegetative preparations (1 mL) of greater than $10^6$ CFU/mL was placed in a 16 mm diameter test tube in a stainless steel basket. Acetic acid (6 mL) was transferred by syringe onto the surface of a cotton ball placed in the basket, which was then loaded into the 600 mL reactor vessel. The reactor vessel was heated to 50° C. and equilibrated with $CO_2$ at atmospheric pressure. The stirring and agitation mechanisms were activated and the reactor vessel pressurized to 3000 psi for 40 minutes. The $CO_2$ pressure was then allowed to drop to 1500 psi at a rate of 300 psi/minute. Agitation was carried out for 1 minute.

After depressurizing the reactor vessel, more acetic acid (4 mL) was introduced at ambient pressure to the additive loop via port 18 (FIG. 1). The loop was sealed and pressurized to 3000 psi. The reactor vessel was the re-pressurized through the additive loop to 3000 psi such that acetic acid was transported into the reactor vessel.

The pressurization/stirring/agitation/depressurization/additive addition process was repeated a total of three times. After the third cycle, a series of three flushing cycles to remove the additive was performed by pressurizing and de-pressurizing the reactor vessel using $CO_2$. The stirring was stopped and the basket was removed from the reactor vessel. The residual CFUs were counted after serial dilution and culturing of both treated and untreated controls.

A log reduction in CFUs of between 6.0 to 6.9 was observed for multiple experimental evaluations using the procedure described above.

EXAMPLE 3B—INVENTION

Example 3A was repeated except that samples containing less than $10^6$ CFU/ml of *B. subtilis* was used. Sterilization resulted in total kill of the *B. subtilis* present. It can therefore be extrapolated from this Example that, had greater than $10^6$ CFU/ml of *B. subtilis* been presented, the sterilization procedure would have resulted in a corresponding 6 log reduction in CFUs.

EXAMPLE 3C—Comparative

Example 3A was repeated except that the acetic acid was added only once at the beginning of the procedure. Although a 6 log reduction in CFUs was not observed, relatively high log reductions of between 4.5 and 4.7 were observed. This data suggests that multiple additions of acetic acid would be needed in order to achieve the desired 6 log reduction in *B. subtilis* CFUs.

EXAMPLE 3D—INVENTION

Example 3A was repeated except that pressure was maintained at a constant 2000 psi rather than cycling Compete kill of bioindicators were observed over multiple tests. These log reductions in CFUs ranged from 6.0 to 7.2.

EXAMPLE 4—INVENTION

Using the equipment and procedure in Example 1, samples of fresh or freeze-dried bone (1 cm×1 cm×0.5 cm) were placed into 16 mm test tubes in a stainless steel basket. Trifluoroacetic acid (4 mL) was transferred by syringe onto the surface of a cotton ball placed in basket, and the basket then loaded into the 600 mL reactor vessel. The reactor vessel was heated to 50° C. and equilibrated with CO2 at atmospheric pressure. The stirring and agitation mechanisms were activated and vessel pressurized to 3000 psi for 40 minutes. Agitation is carried out for 5 minutes. The $CO_2$ pressure was then allowed to drop to 1500 psi at a rate of 300 psi/minute.

The pressurization/stirring/agitation/depressurization process was repeated a total of 3 times. After the third cycle, a series of three flushing cycles to remove the additive was performed by pressurizing and de-pressurizing the reactor vessel using $CO_2$. The stirring was stopped and the basket was removed from the reactor vessel. Bone samples were assayed for sterility and compression strength with the results being that there was sterilization (i.e., $>10^6$ reduction in bacterial spores), and there was no reduction in compression strength attributes.

EXAMPLE 5—INVENTION

To evaluate the efficacy of the improved method for sterilization of bone tissue for implantation, human bone tissue was saturated with a solution containing $10^6$ CFUs/mL of *B. subtilis* spores and subjected to the presented method. The treatments were carried using the following conditions: 4 hours, 60° C., 6 cycles form 3000–1500 psi, constant stirring of SCD, periodic agitation of vessel, addition of 6 mL acetic acid to vessel prior to pressurization, addition of acetic acid (4 mL) per cycle, and ending in two 5 minute flushing cycles.

The sterilized samples and unsterilized controls were assayed for the presence of *B. subtilis* spores by two methods. In the first method, bone was immersed in bacterial media allowing germination and growth of *B. subtilis* spores. Turbidity of media indicated incomplete inactivation while clear media was complete inactivation. When cultured for bacterial growth, none of the bone samples treated with the above method showed detectable turbidity of the culture medium as compared to controls (Table 2).

A sample of sterilized bone tissue was pulverized by grinding under aseptic conditions, then cultured in media. No turbidity was detected, indicating that the sterilization process had permeated the bone tissue (Table 2).

TABLE 2

Sterilization of bone tissue using supercritical carbon dioxide with the presented method

| Bone | Inoculants | Intact Bone Culture | Pulverized Bone Culture |
|---|---|---|---|
| Treated | $10^6$ CFUs/ml of *B. subtilis* spores | No-growth | No-growth |
| Untreated | $10^6$ CFUs/ml of *B. subtilis* spores | Growth | Growth |

EXAMPLE 6A—INVENTION

Example 3D was repeated except that peracetic acid was employed as the sterilization additive. A log reduction in CFUs of between 6.5 to 7.2 was observed for multiple experimental evaluations using the procedure described above.

EXAMPLE 6B—INVENTION

Example 6A was repeated except that pressure was maintained at a constant 2000 psi rather than cycling. Complete kill of bioindicators was observed over multiple tests with log reductions in CFUs ranging from 6.0 to 7.2.

EXAMPLE 7—Comparative

Example 3A was repeated except that the additives listed in Table 3 below were employed under the conditions stated. The results also appear in Table 3.

TABLE 3

| Additive | Temp C. | Time | Quantity (vol. %) | Cycles | Log reduction |
|---|---|---|---|---|---|
| HOCl | 60 | 3 hours | 1.0 | 4 | 0–0.50 |
| Ethanol | 60–50 | 3 hours | 1.0 | 4 | 1.2–4.0 |
| Yeast Extract | 60 | 2 hours | 1.0 | 3 | 0.37–1.1 |
| 50% Citric acid | 60 | 2 hours | 1.0 | 3 | 0.03–0.62 |
| Succinic acid | 50 | 2 hours | 1.0 | 3 | 0.25–0.29 |
| Phosphoric acid | 50 | 2 hours | 1.0 | 3 | 0.18–0.25 |
| Formic acid | 50 | 2 hours | 1.0 | 3 | 0 |
| Malonic acid | 50 | 2 hours | 1.0 | 3 | 0–0.12 |

None of the additives tested in this Example showed efficacy to achieve at least a 6 log reduction in CFUs of *B. stearothermophilus* spores.

EXAMPLE 8—Linearity of Inactivation

Example 2B was repeated except that 4.5% peracetic acid was initially added to the vessel at 0.02 vol. % on a cotton ball and water was added on a separate cotton ball at 1 vol. %. *B. stearothermophilus* spores were inoculated onto glass fiber filters, allowed to dry and packaged into pouches formed of nonwoven fine polyethylene fibers (1073B TYVEK® brand material) and served as bioindicators. Total CFUs per filter were greater than $10^6$. The bioindicators were exposed to differing times of treatment with 4 replicates per time point. The total remaining CFUs were then determined and a plot was generated of log reduction in CFUs over time (FIG. 3). Results revealed that inactivation rates are linear and the time for a single log reduction in the bioindicator packaged in the pouches was 14.24 minutes.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the present invention.

What is claimed is:

1. A sterilization method comprising:
    (a) bringing a material in need of sterilization into contact with a sterilant fluid comprised of carbon dioxide at supercritical pressure and temperature conditions, and a sterilization enhancing effective amount of between about 0.001% to about 2.0% based on the total volume of a chemical sterilization additive, wherein the additive is selected from the group consisting of acetic acid, peracetic acid, trifluoroacetic acid, acetic acid derivatives or mixtures thereof, and
    (b) maintaining said contact with the sterilant fluid under said temperature and pressure conditions while mechanically agitating for a time sufficient to achieve a 6-log reduction or greater in colony forming units (CFUs) of bacterial spores.

2. The sterilization method of claim 1, which comprises agitating the sterilant fluid by stirring.

3. Apparatus for sterilizing an article in need of sterilization through the application of a sterilant fluid comprising:
    a pressure vessel for containing the article in need of sterilization
    a source of supercritical carbon dioxide connected to the pressure vessel;
    a source of a liquid chemical sterilization additive selected from the group consisting of acetic acid, peracetic acid, trifluoroacetic acid, acetic acid derivatives or mixtures thereof connected operatively to the pressure vessel;

means for introducing the supercritical carbon dioxide and sterilization additive to the pressure vessel in an amount of between about 0.001% to about 2.0% of the additive based on a total volume of the sterilant fluid introduced;

means for introducing an article in need of sterilization into the pressure vessel so as to bring the article into contact with the sterilant fluid at supercritical pressure and temperature conditions and maintaining the article in contact with the sterilant fluid under said temperature and pressure conditions while mechanically agitating for a time sufficient to achieve a 6-log reduction or greater in colony forming units (CFUs) of bacterial spores; and a depressurization line fluid-connected to the pressure vessel for evacuating at least some portion of the carbon dioxide and sterilization additive from the pressure vessel so as to depressurize the same.

4. Apparatus as in claim 3, further comprising a liquid-gas separator in said depressurization line for separating carbon dioxide gas from the liquid sterilization additive.

5. Apparatus as in claim 3, further comprising a valve in said depressurization line to allow said at least some portion of the carbon dioxide and sterilization additive to be evacuated from the pressure vessel through the depressurization line.

6. The sterilization method of claim 1, wherein materials treated are selected from the group consisting of thermally or hydrolytically sensitive, medically-important materials.

7. The sterilization method of claim 6, wherein the materials treated are selected from the group consisting of tissue for implantation or transplantation.

8. The sterilization method of claim 6, wherein the materials treated are selected from the group consisting of biodegradable and other medical polymers.

9. The sterilization method of claim 6, wherein the materials treated are selected from the group consisting of drugs, drug delivery systems and/or medical equipment.

* * * * *